(12) United States Patent
Salamone et al.

(10) Patent No.: US 7,632,904 B2
(45) Date of Patent: Dec. 15, 2009

(54) HIGH REFRACTIVE-INDEX, HYDROPHILIC, ARYLSILOXY-CONTAINING MONOMERS AND POLYMERS, AND OPHTHALMIC DEVICES COMPRISING SUCH POLYMERS

(75) Inventors: Joseph C. Salamone, Fairport, NY (US); Jay F. Kunzler, Canandaigua, NY (US); Richard M. Ozark, Solvay, NY (US)

(73) Assignee: Bausch & Lomb Incorporated, Rochester, NY (US)

( * ) Notice: Subject to any disclaimer, the term of this patent is extended or adjusted under 35 U.S.C. 154(b) by 1046 days.

(21) Appl. No.: 11/153,470

(22) Filed: Jun. 15, 2005

(65) Prior Publication Data

US 2006/0286147 A1 Dec. 21, 2006

(51) Int. Cl.
C08F 26/06 (2006.01)
C08F 30/08 (2006.01)
C08F 118/02 (2006.01)

(52) U.S. Cl. ............... 526/258; 526/264; 526/279; 526/303.1; 526/306; 526/319; 526/320; 526/323.1; 526/333; 526/336

(58) Field of Classification Search ............ 526/258, 526/264, 279, 303.1, 306, 319, 320, 323.1, 526/333, 336
See application file for complete search history.

(56) References Cited

U.S. PATENT DOCUMENTS

| 4,327,203 | A | 4/1982 | Deichert et al. |
|---|---|---|---|
| 4,355,147 | A | 10/1982 | Deichert et al. |
| 5,270,418 | A | 12/1993 | Kunzler et al. |
| 5,539,137 | A | 7/1996 | Lewis et al. |
| 5,693,095 | A | 12/1997 | Freeman et al. |
| 5,981,615 | A | 11/1999 | Meijs et al. |
| 6,632,905 | B2 | 10/2003 | Leboeuf |
| 2003/0109661 | A1 | 6/2003 | Salamone et al. |
| 2003/0232951 | A1 | 12/2003 | Friedrich |
| 2004/0068077 | A1 | 4/2004 | Salamone et al. |

FOREIGN PATENT DOCUMENTS

EP 1 455 201 9/2004

OTHER PUBLICATIONS

International Search Report (PCTISA/210) and Written Opinion (PCT/ISA/237) mailed on Oct. 18, 2006.

*Primary Examiner*—Helen L. Pezzuto
(74) *Attorney, Agent, or Firm*—Joseph Barrera

(57) ABSTRACT

Hydrophilic, arylsiloxy-containing monomers and macromonomers have at least a terminal hydrophilic group attached to an arylsiloxy group. The aryl groups attached to siloxy groups can be substituted with other hydrophilic groups. Polymers comprising such hydrophilic, arylsiloxy-containing monomers and macromonomers avoid or reduce the risk of forming vacuoles of absorbed water. Furthermore, such polymers have high refractive index, and, thus, are advantageously used for making ophthalmic devices, such as intraocular lenses, contact lenses, corneal rings, corneal inlays, and keratoprostheses.

14 Claims, No Drawings

HIGH REFRACTIVE-INDEX, HYDROPHILIC, ARYLSILOXY-CONTAINING MONOMERS AND POLYMERS, AND OPHTHALMIC DEVICES COMPRISING SUCH POLYMERS

BACKGROUND OF THE INVENTION

The present invention relates to high refractive-index, hydrophilic, arylsiloxy-containing monomers, macromonomers, and polymers, and ophthalmic devices comprising such polymers.

Since the 1940s ophthalmic devices in the form of intraocular lens ("IOL") implants have been utilized as replacements for diseased or damaged natural ocular lenses. In most cases, an intraocular lens is implanted within an eye at the time of surgically removing the diseased or damaged natural lens, such as for example, in the case of cataracts. For decades, the preferred material for fabricating such intraocular lens implants was poly(methyl methacrylate), which is a rigid, glassy polymer.

Softer, more flexible IOL implants have gained in popularity in more recent years due to their ability to be compressed, folded, rolled or otherwise deformed. Such softer IOL implants may be deformed prior to insertion thereof through an incision in the cornea of an eye. Following insertion of the IOL in an eye, the IOL returns to its original pre-deformed shape due to the memory characteristics of the soft material. Softer, more flexible IOL implants as just described may be implanted into an eye through an incision that is much smaller, i.e., less than 4.0 mm, than that necessary for more rigid IOLs, i.e., 5.5 to 7.0 mm. A larger incision is necessary for more rigid IOL implants because the lens must be inserted through an incision in the cornea slightly larger than the diameter of the inflexible IOL optic portion. Accordingly, more rigid IOL implants have become less popular in the market since larger incisions have been found to be associated with an increased incidence of postoperative complications, such as induced astigmatism.

With recent advances in small-incision cataract surgery, increased emphasis has been placed on developing soft, foldable materials suitable for use in artificial IOL implants. In general, the materials of current commercial IOLs fall into one of three general categories: silicones, hydrophilic acrylics and hydrophobic acrylics.

In general, high water content hydrophilic acrylics, or "hydrogels," have relatively low refractive indices, making them less desirable than other materials with respect to minimal incision size. Low refractive-index materials require a thicker IOL optic portion to achieve a given refractive power. Silicone materials may have a higher refractive index than high-water content hydrogels, but some particular silicone materials tend to unfold explosively after being placed in the eye in a folded position. Explosive unfolding can potentially damage the corneal endothelium and/or rupture the natural lens capsule and associated zonules. Low glass-transition-temperature hydrophobic acrylic materials are desirable because they typically have a high refractive index and unfold more slowly and more controllably than silicone materials. Unfortunately, low glass-transition-temperature hydrophobic acrylic materials, which contain little or no water initially, tend to absorb water over time and form pockets of water or vacuoles in vivo, causing light reflections or "glistenings."

Furthermore, it may be difficult to achieve ideal folding and unfolding characteristics due to the temperature sensitivity of some acrylic polymers.

Because of the noted shortcomings of current polymeric materials available for use in the manufacture of ophthalmic implants, there is a need for stable, biocompatible polymeric materials having desirable physical characteristics and refractive indices.

SUMMARY OF THE INVENTION

In general, the present invention provides hydrophilic, siloxy-containing monomers and macromonomers having high refractive indices and polymeric compositions comprising such monomers or macromonomers.

In one aspect, a monomer or a macromonomer of the present invention has at least an aryl group and at least a hydrophilic group attached directly or indirectly to a silicon atom of a siloxy group, and at least a polymerizable functional group.

In another aspect, a hydrophilic, arylsiloxy-containing monomer of the present invention has a formula of

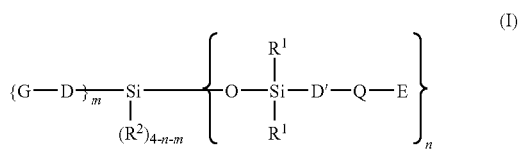

wherein the $R^1$ groups are the same or different and are selected from the group consisting of unsubstituted and substituted $C_6$-$C_{24}$ aromatic groups, saturated straight $C_1$-$C_{10}$ hydrocarbons, unsaturated straight $C_1$-$C_{10}$ hydrocarbons, saturated branched $C_3$-$C_{10}$ hydrocarbons, unsaturated branched $C_3$-$C_{10}$ hydrocarbons, saturated cyclic $C_3$-$C_{10}$ hydrocarbons, unsaturated cyclic $C_3$-$C_{10}$ hydrocarbons, and $C_1$-$C_{10}$ alkyloxy substituents, and at least one $R^1$ group is selected from the group consisting of unsubstituted and substituted $C_6$-$C_{24}$ aromatic groups; $R^2$ are independently selected from the group consisting of hydrogen, saturated straight $C_1$-$C_{10}$ hydrocarbons, unsaturated straight $C_1$-$C_{10}$ hydrocarbons, saturated branched $C_3$-$C_{10}$ hydrocarbons, unsaturated branched $C_3$-$C_{10}$ hydrocarbons, saturated cyclic $C_3$-$C_{10}$ hydrocarbons, unsaturated cyclic $C_3$-$C_{10}$ hydrocarbons, and $C_1$-$C_{10}$ alkyloxy substituents; D and D' are the same or different divalent groups; Q is a divalent group (such as divalent unsubstituted hydrocarbons or substituted hydrocarbons) or an alkyleneoxy or poly(alkyleneoxy) group; each E group is independently selected from the group consisting of unsubstituted and substituted pyrrolidone, hydroxyethyl group, ethoxyethanol group, ethoxymethoxy group, glyceryl group, amides, carboxylic acid, sulfonic acid, phosphonic acid, and alcohols; each G group is independently selected from the group consisting of polymerizable functional groups; n and m are independent integers; $1 \leq n$, $m \leq 3$; and $4-n-m \geq 0$.

In another aspect, the present invention provides a polymerizable hydrophilic, siloxy-containing macromonomer, wherein a plurality of silicon atoms has aromatic side groups.

In still another aspect, a polymerizable hydrophilic, arylsiloxy-containing macromonomer has a formula of

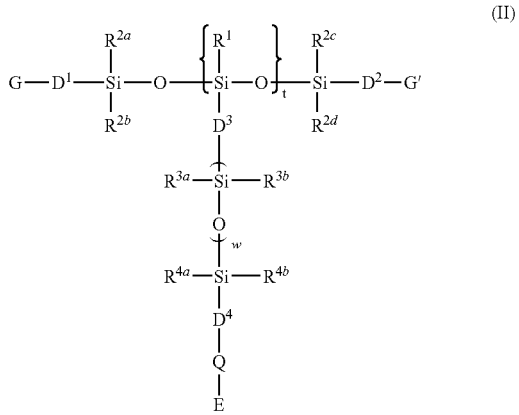

wherein $R^1$, $R^{2a}$, $R^{2b}$, $R^{2c}$, and $R^{2d}$ are independently selected from the group consisting of unsubstituted and substituted $C_6$-$C_{24}$ aromatic groups, saturated straight $C_1$-$C_{10}$ hydrocarbons, unsaturated straight $C_1$-$C_{10}$ hydrocarbons, saturated branched $C_3$-$C_{10}$ hydrocarbons, unsaturated branched $C_3$-$C_{10}$ hydrocarbons, saturated cyclic $C_3$-$C_{10}$ hydrocarbons, unsaturated cyclic $C_3$-$C_{10}$ hydrocarbons, and $C_1$-$C_{10}$ alkyloxy substituents; $R^{3a}$, $R^{3b}$, $R^{4a}$, and $R^{4b}$ are independently selected from the group consisting of unsubstituted and substituted $C_6$-$C_{24}$ aromatic groups; $D^1$, $D^2$, $D^3$, and $D^4$ are independently divalent linking groups; Q is a divalent group, such as divalent hydrocarbon, substituted hydrocarbon, alkyleneoxy, or poly(alkyleneoxy) group; at least a plurality of E groups is independently selected from the group consisting of unsubstituted and substituted pyrrolidone, hydroxyethyl group, ethoxyethanol group, ethoxymethoxy group, glyceryl group, amides, carboxylic acid, sulfonic acid, phosphonic acid, and alcohols; G and G' are independently selected from the group consisting of polymerizable functional groups; t and w are integers; $2 \leq t \leq 500$; and $1 \leq w \leq 100$. In one embodiment, some E groups can be hydrogen or alkyl groups (e.g., alkyl groups having 1-20 carbon atoms, inclusive).

In still another aspect, a polymeric composition comprises a homopolymer of a hydrophilic, arylsiloxy-containing monomer or marcomonomer of the present invention, or a copolymer of at least two hydrophilic, arylsiloxy-containing monomers or macromonomers of the present invention, or a copolymer of a hydrophilic, arylsiloxy-containing monomer or macromonomer of the present invention and at least one other monomer or macromonomer.

In still another aspect, said at least one other monomer is selected from hydrophilic monomers, hydrophobic monomers and macromonomers, and combinations thereof.

In yet another aspect, the present invention provides a method of making a high refractive index hydrophilic, arylsiloxy-containing monomer or macromonomer. The method comprises reacting an arylsiloxy-containing monomer or macromonomer with at least a hydrophilic monomer or macromonomer, such that the resulting compound has a refractive index greater than about 1.4, preferably greater than 1.43.

In yet another aspect, the present invention provides a method of making a hydrophilic polymeric composition having a high refractive index. The method comprises polymerizing a hydrophilic, arylsiloxy-containing monomer or macromonomer, or polymerizing such a monomer or macromonomer and at least a different monomer or macromonomer, such that the refractive index is greater than about 1.4, preferably from about 1.4 to about 1.6. In one embodiment, the refractive index is from about 1.45 to about 1.58.

In yet another aspect, an ophthalmic device comprises a polymeric material that comprises units of at least a hydrophilic, arylsiloxy-containing monomer or macromonomer of the present invention.

Other features and advantages of the present invention will become apparent from the following detailed description and claims.

DETAILED DESCRIPTION OF THE INVENTION

In general, the present invention provides hydrophilic, siloxy-containing monomers and macromonomers having high refractive indices and polymeric compositions comprising such monomers or macromonomers. A monomer or a macromonomer of the present invention has at least a polymerizable functional group, at least an aryl group, and at least a hydrophilic group, each attached directly or indirectly to a silicon atom of a siloxy group. A hydrophilic group can be attached indirectly to a silicon atom through a linking group that can comprise other hydrophobic or hydrophilic groups or a combination thereof. A hydrophilic group also can be attached through another siloxy group. The polymeric compositions of the present invention have refractive index of about 1.4 or greater. In some embodiments, the refractive index is in the range from about 1.4 to about 1.7. In some other embodiments, the refractive index is in the range from about 1.45 to about 1.6.

In one aspect, a polymeric composition of the present invention has an equilibrium water content of greater than about 4.5 percent (by weight), thus avoiding problems related to the formation of water vacuoles. In addition, a polymeric composition of the present invention can have a relatively high elongation, such as about 80 percent or greater. Accordingly, in many aspects, the subject polymeric compositions are more suitable for use in the manufacture of ophthalmic devices than many prior-art polymeric materials.

Current commercial hydrophobic acrylic-based ophthalmic products have water content less than 4.5 percent by weight. These hydrophobic products tend to absorb water over time in vivo and form water vacuoles or "glistenings." In contrast, a polymeric composition comprising units of hydrophilic, arylsiloxy-containing monomers or macromonomers of the present invention tend to absorb water rapidly to equilibrium level. Although applicants do not wish to be bound to any particular theory, it is believed that the absorbed water also is distributed throughout the polymeric composition because of its association with the hydrophilic substituents in the aromatic monomers. Therefore, polymeric compositions of the present invention do not present the risk of formation of water vacuoles in vivo.

In one aspect, a hydrophilic, arylsiloxy-containing monomer of the present invention has a formula of

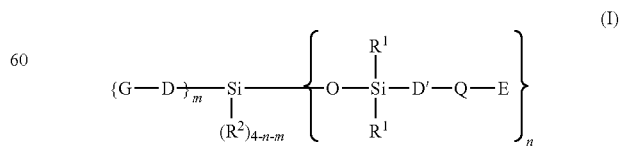

wherein the $R^1$ groups are the same or different and are selected from the group consisting of unsubstituted and substituted $C_6$-$C_{24}$ aromatic groups, saturated straight $C_1$-$C_{10}$ hydrocarbons, unsaturated straight $C_1$-$C_{10}$ hydrocarbons, saturated branched $C_3$-$C_{10}$ hydrocarbons, unsaturated branched $C_3$-$C_{10}$ hydrocarbons, saturated cyclic $C_3$-$C_{10}$ hydrocarbons, unsaturated cyclic $C_3$-$C_{10}$ hydrocarbons, and $C_1$-$C_{10}$ alkyloxy substituents, and at least one $R^1$ group is selected from the group consisting of unsubstituted and substituted $C_6$-$C_{24}$ aromatic groups (preferably, $C_6$-$C_{24}$ aromatic groups substituted with at least a hydrophilic substituent); $R^2$ are independently selected from the group consisting of hydrogen, saturated straight $C_1$-$C_{10}$ hydrocarbons, unsaturated straight $C_1$-$C_{10}$ hydrocarbons, saturated branched $C_3$-$C_{10}$ hydrocarbons, unsaturated branched $C_3$-$C_{10}$ hydrocarbons, saturated cyclic $C_3$-$C_{10}$ hydrocarbons, unsaturated cyclic $C_3$-$C_{10}$ hydrocarbons, and $C_1$-$C_{10}$ alkyloxy substituents; D and D' are the same or different divalent groups (including divalent unsubstituted hydrocarbons, substituted hydrocarbons, alkoxy, arylene, alkyl silyl, or siloxy groups); Q is a divalent group (such as one selected from the group consisting of divalent unsubstituted hydrocarbon, substituted hydrocarbon, alkyleneoxy, or poly(alkyleneoxy) groups); each E group is independently selected from the group consisting of unsubstituted and substituted pyrrolidone, hydroxyethyl group, ethoxyethanol group, ethoxyethylene group, glyceryl group, amides, carboxylic acid, sulfonic acid, phosphonic acid, and alcohols; each G group is independently selected from the group consisting of polymerizable functional groups; n and m are independent integers; $1 \leq n, m \leq 3$; and $4-n-m \geq 0$. In one embodiment, two $R^1$ groups attached to the same silicon atom can be the same, but different from two $R^1$ groups attached to another silicon atom. In another embodiment, all $R^1$ groups are the same.

Non-limiting examples of aromatic groups are phenyl, biphenyl, cumenyl, mesityl, tolyl, xylyl, benzyl, benzhydryl, cinnamyl, phenethyl, styryl, trityl, naphthyl, anthryl, phenanthryl, chrysyl, and derivatives thereof. Preferably, $R^1$ is a $C_6$-$C_{24}$ aromatic group substituted with at least a hydrophilic substituent.

In one embodiment, $R^1$ is a phenyl group; preferably, a phenyl group having at least a hydrophilic substituent.

In another embodiment, $R^1$ is an aromatic other than phenyl; preferably, having at least a hydrophilic substituent.

In another embodiment, at least a hydrophilic substituent on the aromatic group is selected from the group consisting of carboxy, alcohol (including monohydric and polyhydric alcohols), and alkoxy substituents, and combinations thereof.

In another embodiment, at least a hydrophilic substituent on the aromatic group is selected from the group consisting of —COOH, —(CH$_2$)$_2$—CH$_2$OH, —(CHOH)$_2$—CH$_2$OH, —CH$_2$—CHOH—CH$_2$OH, and combinations thereof.

In still another embodiment, at least a hydrophilic substituent on the aromatic group is a poly(alkylene glycol), such as poly(ethylene glycol) having a formula of —(O—CH$_2$—CH$_2$)$_k$OH or —(O—CH$_2$—CH$_2$)$_k$—OCH$_3$, wherein k is an integer and $1 \leq k \leq 100$, preferably $1 \leq k \leq 50$, and more preferably, $1 \leq k \leq 20$.

In a further embodiment, said hydrophilic substituent is selected from the group consisting of carboxamide, dialkyl-substituted carboxamide, amino, quaternary ammonium, alkanolamino, sulfonate, phosphonate, sulfate, phosphate, ureido, substituted sugars, and combinations thereof.

In another embodiment, $R^1$ is selected from the group consisting of hydrogen and saturated straight $C_1$-$C_{10}$ hydrocarbons.

In another aspect, G is a reactive functional group selected from the group consisting of vinyl, allyl, butadienyl, acryloyl, acryloyloxy, methacryloyl, methacryloyloxy, epoxy, itaconyl, maleimido, acrylamido, methacrylamido, fumaryl, styryl, and combinations thereof.

In another aspect, G is selected from the group consisting of vinyl, styryl, acryloyloxy, methacryloyloxy, acrylamido, and methacrylamido.

In another aspect, D and D' are divalent groups independently selected from the group consisting of saturated straight $C_1$-$C_{10}$ hydrocarbons, unsaturated straight $C_1$-$C_{10}$ hydrocarbons, saturated branched $C_3$-$C_{10}$ hydrocarbons, unsaturated branched $C_3$-$C_{10}$ hydrocarbons, saturated cyclic $C_3$-$C_{10}$ hydrocarbons, unsaturated cyclic $C_3$-$C_{10}$ hydrocarbons, and alkyloxy substituents. Preferably, D and D' are saturated straight $C_1$-$C_{10}$ hydrocarbon divalent groups.

In one embodiment, D and D' are the same divalent group of —(CH$_2$)$_x$—, wherein x is an integer in the range from 1 to, and including, 10; e.g., methylene, ethylene, trimethylene, tetramethylene, or pentamethylene.

Q is an alkyleneoxy or a poly(alkyleneoxy) group. Non-limiting examples of Q are ethyleneoxy, propyleneoxy, poly(ethyleneoxy), poly(propyleneoxy), and poly(ethyleneoxy-propyleneoxy). The number of repeating units of such a poly(alkyleneoxy) group can be in the range from 2 to, and including, 100; preferably, from 2 to 50; and more preferably, from 2 to 20.

In one embodiment, a hydrophilic, arylsiloxy-containing monomer of the present invention has a formula

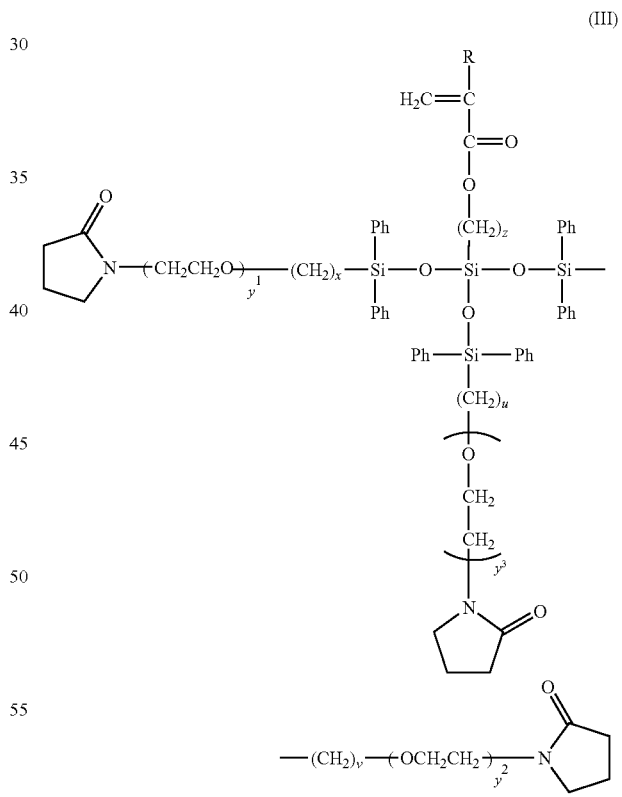

(III)

wherein R is hydrogen or CH$_3$; Ph is unsubstituted or substituted phenyl group; u, v, x, z, $y^1$, $y^2$, and $y^3$ are independently selected integers; $1 \leq u, v, x, Z \leq 10$; and $0 \leq y^1, y^2, y^3 \leq 100$.

In one embodiment, u, v, x, and z are the same and are 1, 2, 3, or 4. In another embodiment, x and v are the same.

In another embodiment, $1 \leq y^1, y^2, y^3 \leq 50$. Alternatively, $1 \leq y^1, y^2, y^3 \leq 20$.

In still another embodiment, Ph is the phenyl group substituted with one or more of the hydrophilic substituents disclosed above for aromatic groups. Non-limiting examples of suitable substituted phenyl groups are represented by

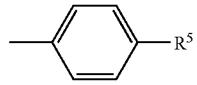

wherein $R^5$ is selected from the group consisting of —COOH, —CH$_2$CH$_2$OH, —CH$_2$CH$_2$OCH$_2$CH$_2$OR (where R is H or CH$_3$), —CH$_2$CH(OH)CH$_2$OH, —C(O)NH$_2$, and —C(O)N(CH$_3$)$_2$.

In another aspect, the present invention provides a polymerizable hydrophilic, arylsiloxy-containing macromonomer having a formula of

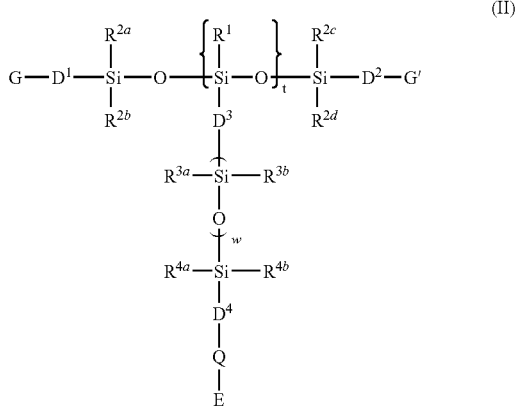

(II)

wherein $R^1$, $R^{2a}$, $R^{2b}$, $R^{2c}$, and $R^{2d}$ are the same or different and are selected from the group consisting of unsubstituted and substituted $C_6$-$C_{24}$ aromatic groups (preferably, $C_6$-$C_{24}$ aromatic groups substituted with at least a hydrophilic substituent), saturated straight $C_1$-$C_{10}$ hydrocarbons, unsaturated straight $C_1$-$C_{10}$ hydrocarbons, saturated branched $C_3$-$C_{10}$ hydrocarbons, unsaturated branched $C_3$-$C_{10}$ hydrocarbons, saturated cyclic $C_3$-$C_{10}$ hydrocarbons, unsaturated cyclic $C_3$-$C_{10}$ hydrocarbons, and $C_1$-$C_{10}$alkyloxy substituents; $R^{3a}$, $R^{3b}$, $R^{4a}$, and $R^{4b}$ are independently selected from the group consisting of unsubstituted and substituted $C_6$-$C_{24}$ aromatic groups (preferably, $C_6$-$C_{24}$ aromatic groups substituted with at least a hydrophilic substituent); $D^1$, $D^2$, $D^3$, and $D^4$ are independently divalent linking groups; Q is a divalent group, such as divalent hydrocarbon, substituted hydrocarbon, alkyleneoxy, or poly(alkyleneoxy) groups; at least a plurality of E groups is independently selected from the group consisting of unsubstituted and substituted pyrrolidone, hydroxyethyl group, ethoxyethanol group, ethoxymethoxy group, glyceryl group, amides, carboxylic acid, sulfonic acid, phosphonic acid, and alcohols; G and G' are independently selected from the group consisting of polymerizable functional groups; t and w are integers; $2 \leq t \leq 500$; and $1 \leq w \leq 100$. In one embodiment, $2 \leq t \leq 200$. In another embodiment, $\leq t \leq 100$. In still another embodiment, $1 \leq w \leq 50$. In still another embodiment, $1 \leq w \leq 20$.

Non-limiting examples of aromatic side groups suitable for $R^1$, $R^{2a}$, $R^{2b}$, $R^{2c}$, $R^{2d}$, $R^{3a}$, $R^{3b}$, $R^{4a}$, and $R^{4b}$ are phenyl, biphenyl, cumenyl, mesityl, tolyl, xylyl, benzyl, benzhydryl, cinnamyl, phenethyl, styryl, trityl, naphthyl, anthryl, phenanthryl, chrysyl, and derivatives thereof. Preferably, such side groups are a $C_6$-$C_{24}$ aromatic group substituted with at least a hydrophilic substituent. In one embodiment, two side groups attached to the same silicon atom can be the same, but different from two side groups attached to another silicon atom. Alternatively, all side groups attached to silicon atoms can be the same.

In one embodiment, $R^{2a}$, $R^{2b}$, $R^{2c}$, $R^{2d}$, $R^{3a}$, $R^{3b}$, $R^{4a}$, and $R^{4b}$ are the phenyl group; preferably, the phenyl group having at least a hydrophilic substituent.

In another embodiment, $R^{2a}$, $R^{2b}$, $R^{2c}$, $R^{2d}$, $R^{3a}$, $R^{3b}$, $R^{4a}$, and $R^{4b}$ are aromatic groups other than phenyl; preferably, having at least a hydrophilic substituent.

In another embodiment, at least a hydrophilic substituent on the aromatic group is selected from the group consisting of carboxy, alcohol (including monohydric and polyhydric alcohols), alkoxy substiuents, and combinations thereof.

In another embodiment, at least a hydrophilic substituent on the aromatic group is selected from the group consisting of —COOH, —(CH$_2$)$_2$—CH$_2$OH, —(CHOH)$_2$—CH$_2$OH, —CH$_2$—CHOH—CH$_2$OH, and combinations thereof.

In still another embodiment, at least a hydrophilic substituent on the aromatic group is a poly(alkylene glycol), such as poly(ethylene glycol) having a formula of —(O—CH$_2$—CH$_2$)$_k$OH or —(O—CH$_2$CH$_2$)$_k$—OCH$_3$, wherein k is an integer and $1 \leq k \leq 100$, preferably $1 \leq k \leq 50$, and more preferably, $1 \leq k \leq 20$.

In a further embodiment, said hydrophilic substituent is selected from the group consisting of carboxamide, dialkyl-substituted carboxamide, amino, alkanolamino, sulfonate, phosphonate, sulfate, phosphate, ureido, substituted sugars, and combinations thereof.

In another aspect, G and G' are reactive functional groups selected from the group consisting of vinyl, allyl, butadienyl, acryloyl, acryloyloxy, methacryloyl, methacryloyloxy, epoxy, itaconyl, maleimido, acrylamido, methacrylamido, fumaryl, styryl, and combinations thereof.

In another aspect, G and G' are selected from the group consisting of vinyl, styryl, acryloyloxy, and methacryloyloxy.

In another aspect, $D^1$, $D^2$, $D^3$, and $D^4$ are divalent groups independently selected from the group consisting of saturated straight $C_1$-$C_{10}$ hydrocarbons, unsaturated straight $C_1$-$C_{10}$ hydrocarbons, saturated branched $C_3$-$C_{10}$ hydrocarbons, unsaturated branched $C_3$-$C_{10}$ hydrocarbons, saturated cyclic $C_3$-$C_{10}$ hydrocarbons, unsaturated cyclic $C_3$-$C_{10}$ hydrocarbons, and alkyloxy substituents. Preferably, $D^1$, $D^2$, $D^3$, and $D^4$ are independently selected from the group consisting of saturated straight $C_1$-$C_{10}$ hydrocarbon divalent groups.

In one embodiment, $D^1$, $D^2$, $D^3$, and $D^4$ are the same divalent group of —(CH$_2$)$_x$—, wherein x is an integer in the range from 1 to, and including, 10; e.g., methylene, ethylene, trimethylene, tetramethylene, or pentamethylene.

Q is an alkyleneoxy or a poly(alkyleneoxy) group. Non-limiting examples of Q are ethyleneoxy, propyleneoxy, poly(ethyleneoxy), poly(propyleneoxy), and poly(ethylenepropyleneoxy). The number of repeating units of such a poly(alkyleneoxy) group can be in the range from 2 to, and including, 100; preferably, from 2 to 50; and more preferably, from 2 to 20.

Hydrophilic, arylsiloxy-containing monomers and macromonomers of the present invention can be used to produce homopolymers or copolymers having high refractive indices, such as for example about 1.4 or greater. In some embodiments, the homopolymers or copolymers have refractive indices in the range from about 1.4 to about 1.7; in some other embodiments, from about 1.45 to about 1.6.

Alternatively, a hydrophilic, arylsiloxy-containing monomer or macromonomer of the present invention can be copolymerized with another hydrophilic or hydrophobic monomer to provide a polymer having high refractive index, such as about 1.4 or greater.

Non-limiting examples of other hydrophilic monomers useful for polymerization with one or more hydrophilic, arylsiloxy-containing monomers or macromonomers of the present invention include N,N'-dimethylacrylamide, glycerol methacrylate, N-vinylpyrrolidone, and 2-hydroxyethyl methacrylate. Preferably, N,N'-dimethylacrylamide is used for increased hydrophilicity.

Non-limiting examples of other hydrophobic monomers useful for polymerization with one or more hydrophilic, arylsiloxy-containing monomers of the present invention include $C_1$-$C_{10}$ alkyl methacrylates (e.g., methyl methacrylate, ethyl methacrylate, propyl methacrylate, butyl methacrylate, octyl methacrylate, or 2-ethylhexyl methacrylate; preferably, methyl methacrylate to control mechanical properties), $C_1$-$C_{10}$ alkyl acrylates (e.g., methyl acrylate, ethyl acrylate, propyl acrylate, or hexyl acrylate; preferably, butyl acrylate to control mechanical properties), $C_6$-$C_{40}$ arylalkyl acrylates (e.g., 2-phenylethyl acrylate, benzyl acrylate, 3-phenylpropyl acrylate, 4-phenylbutyl acrylate, 5-phenylpentyl acrylate, 8-phenyloctyl acrylate, or 2-phenylethoxy acrylate; preferably, 2-phenylethyl acrylate to increase refractive index), and $C_6$-$C_{40}$ arylalkyl methacrylates (e.g., 2-phenylethyl methacrylate, 3-phenylpropyl methacrylate, 4-phenylbutyl methacrylate, 5-phenylpentyl methacrylate, 8-phenyloctyl methacrylate, 2-phenoxyethyl methacrylate, 3,3-diphenylpropyl methacrylate, 2-(1-naphthylethyl) methacrylate, benzyl methacrylate, or 2-(2-naphthylethyl) methacrylate; preferably, 2-phenylethyl methacrylate to increase refractive index). Other suitable hydrophobic monomers include silicon-containing monomers, especially aromatic-based silicon-containing monomer, such as 3-methacryloyloxypropyldiphenylmethylsilane.

An embodiment of the hydrophilic, arylsiloxy-containing monomer having Formula (III) can be produced by a method illustrated in Scheme 1. In the following reaction schemes, Ph represents an unsubstituted or substituted phenyl group.

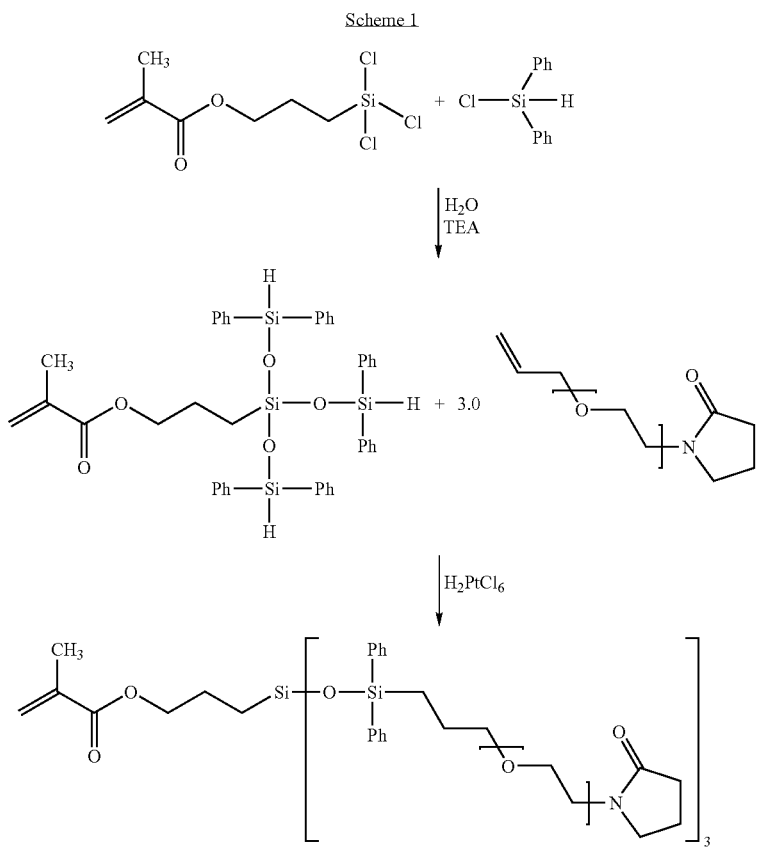

Another embodiment of the hydrophilic, arylsiloxy-containing monomer of the present invention can be produced by a method illustrated in Scheme 2.

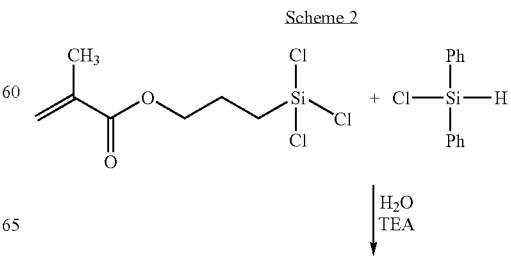

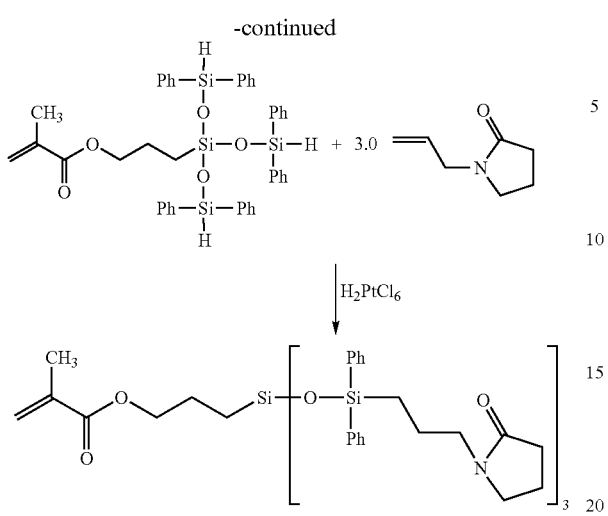

Another embodiment of the hydrophilic, arylsiloxy-containing monomer of the present invention can be produced by a method illustrated in Scheme 3.

In one aspect, a method for producing a polymerizable, hydrophilic, arylsiloxy-containing monomer of the present invention comprises: (a) providing an arylsiloxy-containing compound having the polymerizable group and at least a hydrosilyl group, and a hydrophilic compound having a hydrophilic group and a functional group that is capable of reacting with the hydrosilyl group; and (b) reacting the arylsiloxy-containing compound and the hydrophilic compound under conditions and for a time sufficient to produce the polymerizable, hydrophilic, arylsiloxy-containing monomer.

An embodiment of hydrophilic, arylsiloxy-containing macromonomers of the present invention, as represented by Formula (IV), can be produced by a method illustrated in Scheme 4. In Formula (IV), Ph is an unsubstituted or substituted phenyl group; and p, q, r, s, and w are integers greater than or equal to 1; and t is an integer greater than 1.

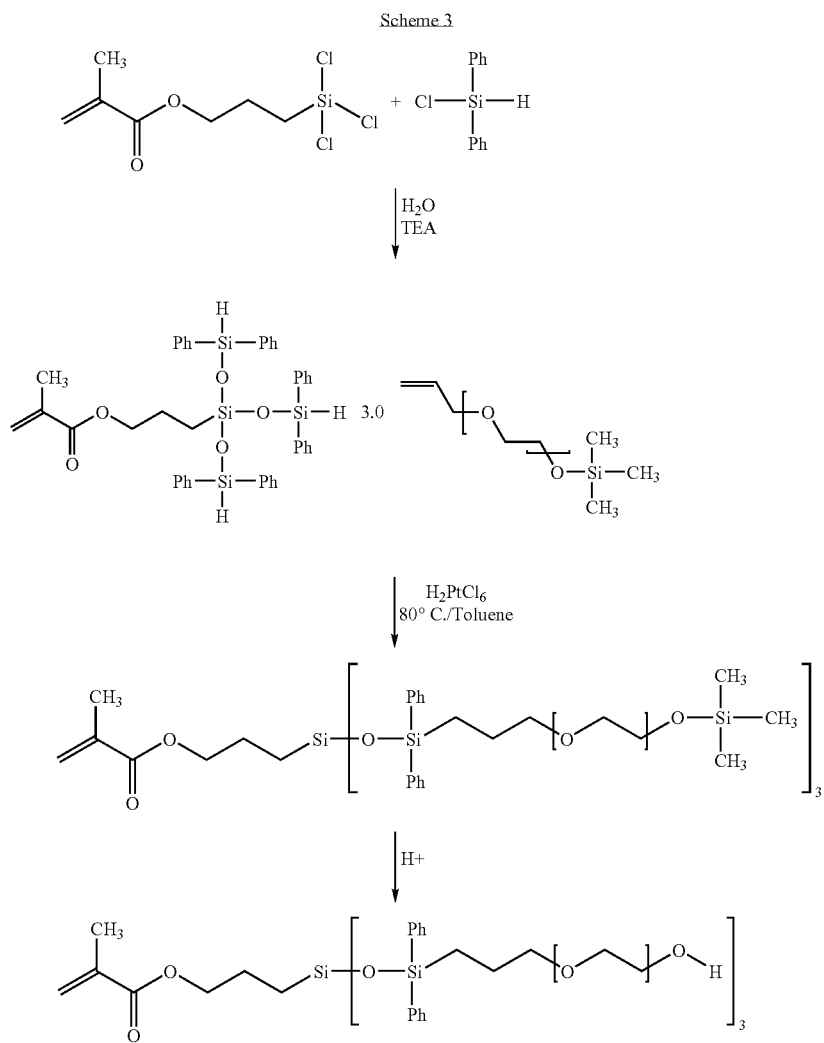

Scheme 4

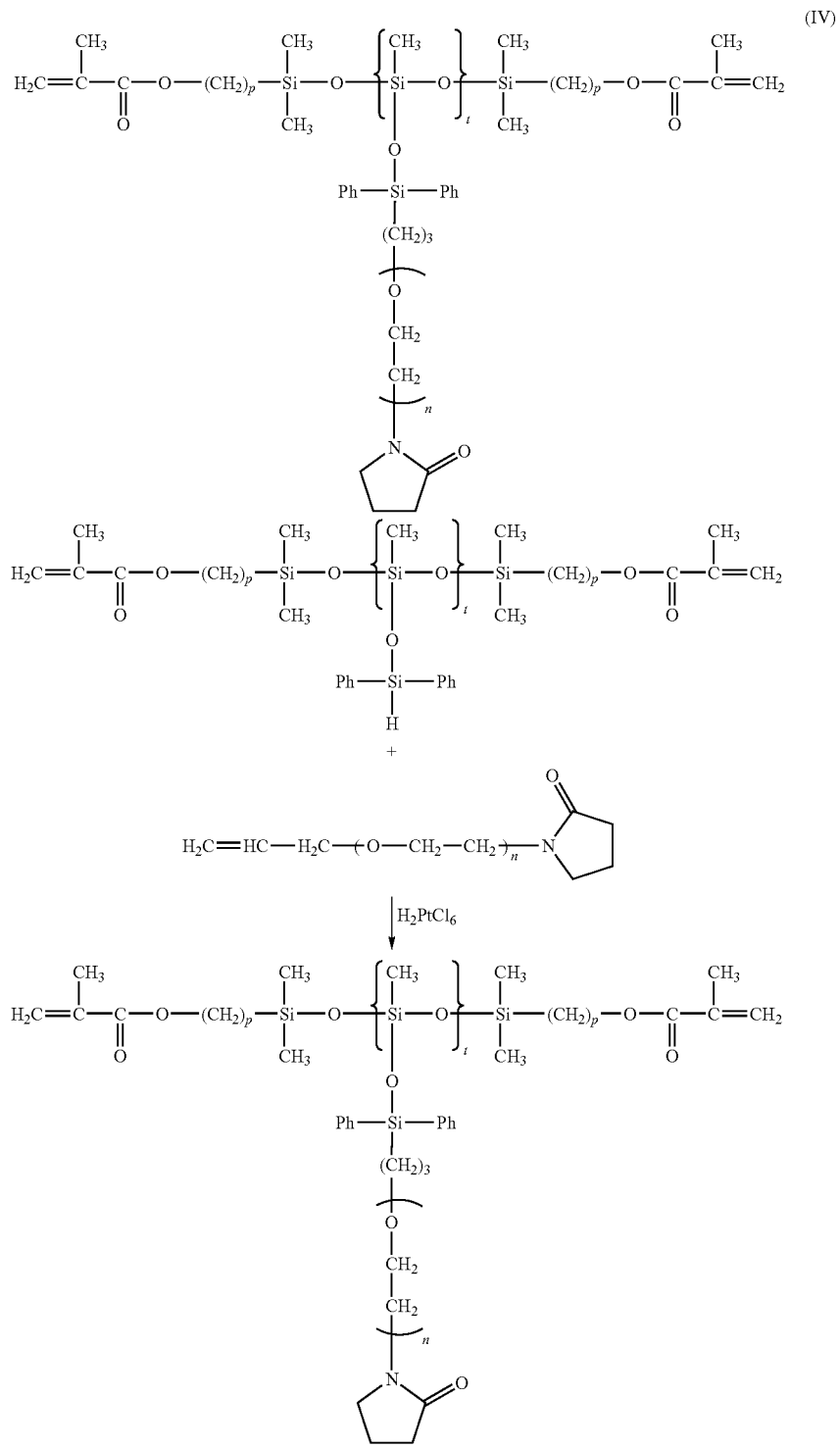

In one aspect, a method for producing a hydrophilic, arylsiloxy-containing macromonomer of the present invention comprises: (a) providing an arylsiloxy-containing macromonomer having a plurality of hydrosilyl groups, and at least a hydrophilic compound having a hydrophilic group and a functional group that is capable of reacting with the hydrosilyl groups; and (b) reacting the arylsiloxy-containing macromonomer and the hydrophilic compound under conditions and for a time sufficient to produce the hydrophilic, arylsiloxy-containing macromonomer.

Homopolymers of a hydrophilic, arylsiloxy-containing monomer or macromonomer of the present invention and copolymers comprising one or more hydrophilic, arylsiloxy-containing monomers or macromonomers of the present invention and at least another monomer can be produced by free radical polymerization. For example, the polymerization of the hydrophilic, arylsiloxy-containing monomer having Formula (III) and 2-phenylethyl methacrylate (or 2-phenylethyl acrylate) can be carried out in the presence of a thermal polymerization initiator (such as one selected from the list of thermal polymerization initiators disclosed below) at a temperature in the range from about 20° C. to about 120° C. Alternatively, the polymerization can be carried out in the presence of a photoinitiator selected from the list of photoinitiators disclosed below at a temperature in the range from about 20° C. to about 60° C. A desired molar ratio of the monomers can be chosen and a desired molecular weight can be achieved by a skilled artisan. For example, the number of repeating units of each type of monomer can be in the range from about 1 to about 100,000, or from 1 to about 50,000, or from 1 to about 20,000, or from 1 to about 5,000.

Another exemplary hydrophilic copolymer comprises the monomer having Formula (III); N,N'-dimethylacrylamide; and 2-phenylethyl methacrylate (or 2-phenylethyl acrylate). The polymerization reaction can be carried out in the presence of a thermal polymerization initiator (such as one selected from the list of thermal polymerization initiators disclosed below) at a temperature in the range from about 20° C. to about 120° C. Alternatively, the reaction can be carried out in the presence of a photoinitiator selected from the list of photoinitiators disclosed below at a temperature in the range from about 20° C. to about 60° C. A desired molar ratio of the monomers can be chosen and a desired molecular weight can be achieved by a skilled artisan. For example, the number of repeating units of each of the monomers can be in the range from about 1 to about 100,000, or from 1 to about 50,000, or from 1 to 20,000.

A formulation for the production of a polymer comprising a hydrophilic, arylsiloxy-containing monomer or macromonomer of the present invention can include one or more crosslinking agents in an amount less than about 10 percent by weight of the weight of all monomers and crosslinking agents, if desired. In one embodiment, the crosslinking agents are present in an amount less than about 5 percent by weight. In another embodiment, the crosslinking agents are present in an amount less than about 2 percent by weight.

Non-limiting examples of suitable crosslinking agents include ethylene glycol dimethacrylate ("EGDMA"); diethylene glycol dimethacrylate; ethylene glycol diacrylate; triethylene glycol dimethacrylate; triethylene diacrylate; allyl methacrylates; allyl acrylates; 1,3-propanediol dimethacrylate; 1,3-propanediol diacrylate; 1,6-hexanediol dimethacrylate; 1,6-hexanediol diacrylate; 1,4-butanediol dimethacrylate; 1,4-butanediol diacrylate; trimethylolpropane trimethacrylate ("TMPTMA"); glycerol trimethacrylate; poly(ethyleneoxide mono- and di-acrylate); N,N'-dihydroxyethylene bisacrylamide; diallyl phthalate; triallyl cyanurate; divinylbenzene; ethylene glycol divinyl ether; N,N'-methylene-bis-(meth)acrylamide; divinylbenzene; divinylsulfone; and the like.

Although not required, homopolymers or copolymers within the scope of the present invention may optionally have one or more strengthening agents added prior to polymerization, preferably in quantities of less than about 80 weight percent but more typically from about 20 to about 60 weight percent. Non-limiting examples of suitable strengthening agents are described in U.S. Pat. Nos. 4,327,203; 4,355,147; and 5,270,418; each of which is incorporated herein in its entirety by reference. Specific examples, not intended to be limiting, of such strengthening agents include cycloalkyl acrylates and methacrylates; e.g., tert-butylcyclohexyl methacrylate and isopropylcyclopentyl acrylate.

One or more ultraviolet ("UV") light absorbers may optionally be added to the copolymers prior to polymerization in quantities less than about 5 percent by weight. Suitable UV light absorbers for use in the present invention include for example, but are not limited to, β-(4-benzotriazoyl-3-hydroxyphenoxy)ethyl acrylate; 4-(2-acryloxyethoxy)-2-hydroxybenzophenone; 4-methacryloyloxy-2-hydroxybenzophenone; 2-(2'-methacryloyloxy-5'-methylphenyl) benzotriazole; 2-(2'-hydroxy-5'-methacryloyloxyethyl phenyl)-2H-benzotriazole; 2-[3'-tert-butyl-2'-hydroxy-5'-(3''-methacryloyloxypropyl)phenyl]-5-chlorobenzotriazole; 2-(3'-tert-butyl-5'-(3''-dimethylvinylsilylpropoxy)-2'-hydroxyphenyl]-5-methoxybenzotriazole; 2-(3'-allyl-2'-hydroxy-5'-methylphenyl)benzotriazole; 2-[3'-tert-butyl-2'-hydroxy-5'-(3''-methacryloyloxypropoxy)phenyl]-5-methoxybenzotriazole, and 2-[3'-tert-butyl-2'-hydroxy-5'-(3''-methacryloyloxypropoxy)phenyl]-5-chlorobenzotriazole. Preferably, the UV light absorber also has a polymerizable functional group. In one embodiment, the preferred UV light absorbers are β-(4-benzotriazoyl-3-hydroxyphenoxy)ethyl acrylate and 2-[3'-tert-butyl-2'-hydroxy-5'-(3''-methacryloyloxypropoxy)phenyl]-5-chlorobenzotriazole.

One or more suitable free radical polymerization initiators may be desirably added to the copolymers of the present invention. These initiators include thermal polymerization initiators and photopolymerization initiators. Thermal polymerization initiators include organic peroxy compounds and azobis(organonitrile) compounds. Non-limiting examples of suitable organic peroxy compounds include peroxymonocarbonate esters, such as tert-butylperoxy isopropyl carbonate; peroxydicarbonate esters, such as di(2-ethylhexyl) peroxydicarbonate, di(sec-butyl) peroxydicarbonate, and diisopropyl peroxydicarbonate; diacyl peroxides, such as 2,4-dichlorobenzoyl peroxide, isobutyryl peroxide, decanoyl peroxide, lauroyl peroxide, propionyl peroxide, acetyl peroxide, benzoyl peroxide, p-chlorobenzoyl peroxide; peroxyesters, such as ter-butylperoxy pivalate, tert-butylperoxy octylate, and tert-butylperoxy isobutyrate; methylethylketone peroxide; and acetylcyclohexane sulfonyl peroxide. Non-limiting examples of suitable azobis(organonitrile) compounds include azobis(isobutyronitrile); 2,2'-azobis(2,4-dimethylpentanenitrile); 1,1'-azobiscyclohexanecarbonitrile; and azobis(2,4-dimethylvaleronitrile); and mixtures thereof. Preferably, such an initiator is employed in a concentration of approximately 0.01 to 1 percent by weight of the total monomer mixture.

Representative UV photopolymerization initiators include those known in the field, such as the classes of benzophenone and its derivatives, benzoin ethers, and phosphine oxides. Some non-limiting examples of these initiators are benzophenone; 4,4'-bis(dimethylamino)benzophenone; 4,4'-dihydroxybenzophenone; 2,2-diethoxyacetophenone; 2,2-dimethoxy-2-phenylacetophenone; 4-(dimethylamino) benzophenone; 2,5-dimethylbenzophenone; 3,4-dimethybenzophenone; 4'-ethoxyacetophenone; 3'-hydroxyacetophenone; 4'-hydroxyacetophenone; 3-hydroxybenzophenone; 4-hydroxybenzophenone; 1-hydroxycyclohexyl phenyl ketone; 2-hydroxy-2-methylpropiophenone; 2-methylbenzophenone; 3-methylbenzophenone; 4'-phenoxyacetophenone; 2-methyl-4'-(methylthio)-2-morpholinopropiophenone; benzoin methyl ether; benzoin ethyl ether; diphenyl(2,4,6-trimethylbenzoyl)phosphine oxide. These initiators are commercially available from Sigma-Aldrich. Other photo polymerization initiators are known under the trade names Darocur™ and Irgacure™, such as Darocur™ 1173 (2-hydroxy-2-methyl-1-phenyl-1-propanone), Irgacure™ 651 (2,2-dimethoxy-2-phenylacetophenone), Irgacure™ 819 (phenyl-bis(2,4,6-trimethyl benzoyl) phosphine oxide), and Irgacure™ 184 (1-hydroxy cyclohexyl phenyl ketone) from Ciba-Geigy, Basel, Switzerland.

The polymeric compositions of the present invention are transparent, flexible, of relatively high refractive index and of relatively high elongation. The polymeric compositions of the present invention with the desirable physical properties noted above are particularly useful in the manufacture of ophthalmic devices such as, but not limited to, relatively thin, foldable IOLs, contact lenses, corneal rings, corneal inlays, and keratoprostheses. Furthermore, absorbed water in the polymeric compositions of the present invention does not tend to form water vacuoles. Thus, the polymeric compositions of the present invention are more advantageously used in ophthalmic device applications than prior-art acrylic compositions.

IOLs having relatively thin optic portions are critical in enabling a surgeon to minimize surgical incision size. Keeping the surgical incision size to a minimum reduces intraoperative trauma and postoperative complications. A relatively thin IOL optic portion is also critical for accommodating certain anatomical locations in the eye such as the anterior chamber and the ciliary sulcus. IOLs may be placed in the anterior chamber for increasing visual acuity in either aphakic or phakic eyes, or placed in the ciliary sulcus for increasing visual acuity in phakic eyes.

The polymeric compositions of the present invention have the flexibility required to allow implants manufactured from the same to be folded or deformed for insertion into an eye through the smallest possible surgical incision, i.e., 3.5 mm or smaller.

In general, a method of making an ophthalmic device comprises: (a) providing a polymerizable composition comprising a hydrophilic, arylsiloxy-containing monomer or macromonomer of the present invention; and (b) curing the polymerizable composition under conditions and for a time sufficient to produce the ophthalmic device. The curing can be carried out such that the polymerizable composition is solidified into the final form of the ophthalmic device or such that a solid article is first produced and the ophthalmic device is further shaped therefrom.

In one embodiment, the method of making an ophthalmic device comprises: (a) providing a polymerizable composition comprising a hydrophilic, arylsiloxy-containing monomer or macromonomer; (b) disposing the polymerizable composition in a mold cavity, which forms a shape of the ophthalmic device; and (c) curing the polymerizable composition under a condition and for a time sufficient to form the ophthalmic device; wherein the hydrophilic, arylsiloxy-containing monomer has a formula of

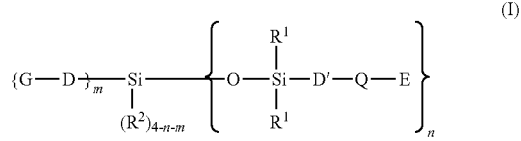

(I)

wherein the $R^1$ groups are the same or different and are selected from the group consisting of unsubstituted and substituted $C_6$-$C_{24}$ aromatic groups, saturated straight $C_1$-$C_{10}$ hydrocarbons, unsaturated straight $C_1$-$C_{10}$ hydrocarbons, saturated branched $C_3$-$C_{10}$ hydrocarbons, unsaturated branched $C_3$-$C_{10}$ hydrocarbons, saturated cyclic $C_3$-$C_{10}$ hydrocarbons, unsaturated cyclic $C_3$-$C_{10}$ hydrocarbons, and $C_1$-$C_{10}$ alkyloxy substituents, and at least one $R^1$ group is selected from the group consisting of unsubstituted and substituted $C_6$-$C_{24}$ aromatic groups (preferably, $C_6$-$C_{24}$ aromatic groups substituted with at least a hydrophilic substituent); $R^2$ are independently selected from the group consisting of hydrogen, saturated straight $C_1$-$C_{10}$ hydrocarbons, unsaturated straight $C_1$-$C_{10}$ hydrocarbons, saturated branched $C_3$-$C_{10}$ hydrocarbons, unsaturated branched $C_3$-$C_{10}$ hydrocarbons, saturated cyclic $C_3$-$C_{10}$ hydrocarbons, unsaturated cyclic $C_3$-$C_{10}$ hydrocarbons, and $C_1$-$C_{10}$ alkyloxy substituents; D and D' are the same or different divalent groups; Q is a divalent group (such as a divalent unsubstituted hydrocarbon, substituted hydrocarbon, alkyleneoxy, or poly(alkyleneoxy) group); each E group is independently selected from the group consisting of unsubstituted and substituted pyrrolidone, hydroxyethyl group, ethoxyethanol group, ethoxymethoxy group, glyceryl group, amides, carboxylic acid, sulfonic acid, phosphonic acid, and alcohols; each G group is independently selected from the group consisting of polymerizable functional groups; n and m are independent integers; $1 \leq n$, $m \leq 3$; and $4-n-m \geq 0$; and wherein the hydrophilic, arylsiloxy-containing macromonomer has a formula of

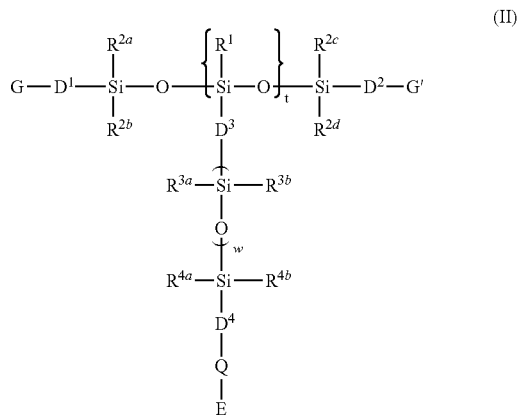

(II)

wherein $R^1$, $R^{2a}$, $R^{2b}$, $R^{2c}$, and $R^{2d}$ are the same or different and are selected from the group consisting of unsubstituted and substituted $C_6$-$C_{24}$ aromatic groups (preferably, $C_6$-$C_{24}$ aromatic groups substituted with at least a hydrophilic substituent), saturated straight $C_1$-$C_{10}$ hydrocarbons, unsaturated straight $C_1$-$C_{10}$ hydrocarbons, saturated branched $C_3$-$C_{10}$ hydrocarbons, unsaturated branched $C_3$-$C_{10}$ hydrocarbons, saturated cyclic $C_3$-$C_{10}$ hydrocarbons, unsaturated cyclic $C_3$-$C_{10}$ hydrocarbons, and $C_1$-$C_{10}$ alkyloxy substituents; $R^{3a}$, $R^{3b}$, $R^{4a}$, and $R^{4b}$ are independently selected from the group consisting of unsubstituted and substituted $C_6$-$C_{24}$ aromatic groups (preferably, $C_6$-$C_{24}$ aromatic groups substituted with at least a hydrophilic substituent); $D^1$, $D^2$, $D^3$, and $D^4$ are independently divalent linking groups; Q is a divalent group, such as divalent hydrocarbon, substituted hydrocarbon, alkyleneoxy, or poly(alkyleneoxy) group; at least a plurality of E groups is independently selected from the group consisting of unsubstituted and substituted pyrrolidone, hydroxyethyl group, ethoxyethanol group, ethoxymethoxy group, glyceryl group, amides, carboxylic acid, sulfonic acid, phosphonic acid, and alcohols; G and G' are independently selected from the group consisting of polymerizable functional groups; t and w are integers; $2 \leq t \leq 500$; and $1 \leq w \leq 100$. In one embodiment, $2 \leq t \leq 200$. In another embodiment, $\leq t \leq 100$. In still another embodiment, $1 \leq w \leq 50$. In still another embodiment, $1 \leq w \leq 20$.

In one embodiment of the method, at least a hydrophilic substituent on the aromatic group is selected from the group consisting of carboxy, carboxamide, alcohol (including monohydric and polyhydric alcohols) substituents, and combinations thereof.

In another embodiment of the method, at least a hydrophilic substituent on the aromatic group is selected from the group consisting of —COOH, —(CH$_2$)$_2$—CH$_2$OH, —(CHOH)$_2$—CH$_2$OH, —CH$_2$—CHOH—CH$_2$OH, and combinations thereof.

In still another embodiment, at least a hydrophilic substituent on the aromatic group is a poly(alkylene glycol), such as poly(ethylene glycol) having a formula of —(O—CH$_2$—CH$_2$)$_k$OH or —(O—CH$_2$—CH$_2$)$_k$—OCH$_3$, wherein k is an integer and $1 \leq k \leq 100$, preferably $1 \leq k \leq 50$, and more preferably, $1 \leq k \leq 20$.

In a further embodiment, said hydrophilic substituent is selected from the group consisting of carboxamide, dialkyl-substituted carboxamide, amino, quaternary ammonium, alkanolamino, sulfonate, phosphonate, sulfate, phosphate, ureido, substituted sugars, and combinations thereof.

In yet another embodiment, the polymerizable composition also comprises a crosslinking agent, or a polymerization initiator, or both. The polymerization initiator is preferably a thermal polymerization initiator. The curing can be carried out at an elevated temperature such as in the range from about ambient temperature to about 120° C. In some embodiments, the curing is carried out at a temperature in the range from slightly higher than ambient temperature to about 100° C. A time from about 1 minute to about 48 hours is typically adequate for the curing. In some instances, adequate curing time can be achieved in the range from about 10 minutes to about 10 hours. In still some other instances, adequate curing time is in the range from about 20 minutes to about 5 hours.

In another embodiment, the method of making an ophthalmic device comprises: (a) providing polymerizable composition comprising a hydrophilic, arylsiloxy-containing monomer or a macromonomer; (b) casting the polymerizable composition under a condition and for a time sufficient to form a solid block; and (c) shaping the block into the ophthalmic device; wherein the hydrophilic, arylsiloxy-containing monomer has a formula of

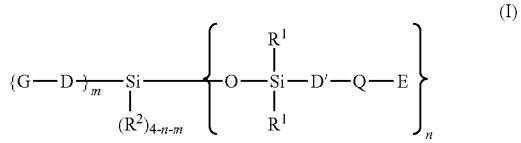

(I)

wherein the R$^1$ groups are the same or different and are selected from the group consisting of unsubstituted and substituted C$_6$-C$_{24}$ aromatic groups, saturated straight C$_1$-C$_{10}$ hydrocarbons, unsaturated straight C$_1$-C$_{10}$ hydrocarbons, saturated branched C$_3$-C$_{10}$ hydrocarbons, unsaturated branched C$_3$-C$_{10}$ hydrocarbons, saturated cyclic C$_3$-C$_{10}$ hydrocarbons, unsaturated cyclic C$_3$-C$_{10}$ hydrocarbons, and C$_1$-C$_{10}$ alkyloxy substituents, and at least one R$^1$ group is selected from the group consisting of unsubstituted and substituted C$_6$-C$_{24}$ aromatic groups (preferably, C$_6$-C$_{24}$ aromatic groups substituted with at least a hydrophilic substituent); R$^2$ are independently selected from the group consisting of hydrogen, saturated straight C$_1$-C$_{10}$ hydrocarbons, unsaturated straight C$_1$-C$_{10}$ hydrocarbons, saturated branched C$_3$-C$_{10}$ hydrocarbons, unsaturated branched C$_3$-C$_{10}$ hydrocarbons, saturated cyclic C$_3$-C$_{10}$ hydrocarbons, unsaturated cyclic C$_3$-C$_{10}$ hydrocarbons, and C$_1$-C$_{10}$ alkyloxy substituents; D and D' are the same or different divalent group; Q is a divalent group (such as divalent unsubstituted hydrocarbon, substituted hydrocarbon, alkyleneoxy, or poly(alkyleneoxy) group); each E group is independently selected from the group consisting of unsubstituted and substituted pyrrolidone, hydroxyethyl group, ethoxyethanol group, ethoxymethoxy group, glyceryl group, amides, carboxylic acid, sulfonic acid, phosphonic acid, and alcohols; each G group is independently selected from the group consisting of polymerizable functional groups; n and m are independent integers; $1 \leq n$, $m \leq 3$; and $4-n-m \geq 0$; and wherein the macromonomer has a formula of

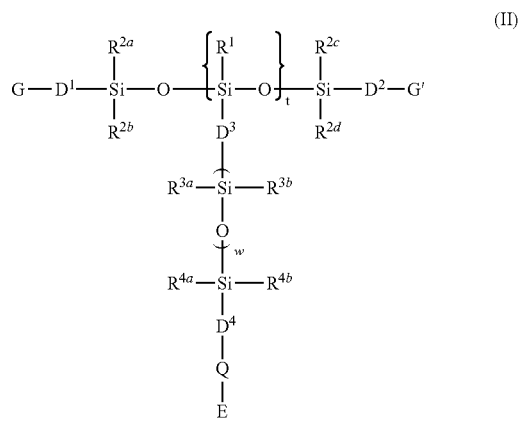

(II)

wherein R$^1$, R$^{2a}$, R$^{2b}$, R$^{2c}$, and R$^{2d}$ are the same or different and are selected from the group consisting of unsubstituted and substituted C$_6$-C$_{24}$ aromatic groups (preferably, C$_6$-C$_{24}$ aromatic groups substituted with at least a hydrophilic substituent), saturated straight C$_1$-C$_{10}$ hydrocarbons, unsaturated straight C$_1$-C$_{10}$ hydrocarbons, saturated branched C$_3$-C$_{10}$ hydrocarbons, unsaturated branched C$_3$-C$_{10}$ hydrocarbons, saturated cyclic C$_3$-C$_{10}$ hydrocarbons, unsaturated cyclic C$_3$-C$_{10}$ hydrocarbons, and C$_1$-C$_{10}$ alkyloxy substituents; R$^{3a}$, R$^{3b}$, R$^{4a}$, and R$^{4b}$ are independently selected from the group consisting of unsubstituted and substituted C$_6$-C$_{24}$ aromatic groups (preferably, C$_6$-C$_{24}$ aromatic groups substituted with at least a hydrophilic substituent); D$^1$, D$^2$, D$^3$, and D$^4$ are independently divalent linking groups; Q is a divalent group, such as divalent hydrocarbon, substituted hydrocarbon, alkyleneoxy, or poly(alkyleneoxy) group; at least a plurality of E groups is independently selected from the group consisting of unsubstituted and substituted pyrrolidone, hydroxyethyl group, ethoxyethanol group, ethoxymethoxy group, glyceryl group, amides, carboxylic acid, sulfonic acid, phosphonic acid, and alcohols; G and G' are independently selected from the group consisting of polymerizable functional groups; t and w are integers; $2 \leq t \leq 500$; and $1 \leq w \leq 100$. In one embodiment, $2 \leq t \leq 200$. In another embodiment, $\leq t \leq 100$. In still another embodiment, $1 \leq w \leq 50$. In still another embodiment, $1 \leq w \leq 20$.

In one embodiment, said at least a hydrophilic substituent is selected from the group consisting of carboxy, alcohols (including monohydric and polyhydric alcohols), and combinations thereof.

In another embodiment, at least a hydrophilic substituent on the aromatic group is selected from the group consisting of —COOH, —(CH$_2$)$_2$—CH$_2$OH, —(CHOH)$_2$—CH$_2$OH, —CH$_2$—CHOH—CH$_2$OH, and combinations thereof.

In still another embodiment, at least a hydrophilic substituent on the aromatic group is a poly(alkylene glycol), such as poly(ethylene glycol) having a formula of —(O—CH$_2$—CH$_2$)$_k$OH or —(O—CH$_2$—CH$_2$)$_k$—OCH$_3$, wherein k is an integer and $1 \leq k \leq 100$, preferably $1 \leq k \leq 50$, and more preferably, $1 \leq k \leq 20$.

In a further embodiment, said hydrophilic substituent is selected from the group consisting of carboxamide, dialkyl-substituted carboxamide, amino, alkanolamino, sulfonate, phosphonate, sulfate, phosphate, ureido, substituted sugars, and combinations thereof.

In yet another embodiment, the polymerizable composition also comprises a crosslinking agent, or a polymerization initiator, or both. The polymerization initiator is preferably a thermal polymerization initiator. The casting can be carried out at an elevated temperature such as in the range from about 20° C. to about 120° C. In some embodiments, the casting is carried out at a temperature from slightly higher than ambient temperature to about 100° C. A time from about 1 minute to about 48 hours is typically adequate for the polymerization. The shaping can comprise cutting the solid block into wafers, and lathing or machining the wafers into the shape of the final ophthalmic device.

Ophthalmic medical devices manufactured using polymeric compositions of the present invention are used as customary in the field of ophthalmology. For example, in a surgical cataract procedure, an incision is placed in the cornea of an eye. Through the corneal incision the cataractous natural lens of the eye is removed (aphakic application) and an IOL is inserted into the anterior chamber, posterior chamber or lens capsule of the eye prior to closing the incision. However, the subject ophthalmic devices may likewise be used in accordance with other surgical procedures known to those skilled in the field of ophthalmology.

While specific embodiments of the present invention have been described in the foregoing, it will be appreciated by those skilled in the art that many equivalents, modifications, substitutions, and variations may be made thereto without departing from the spirit and scope of the invention as defined in the appended claims.

What is claimed is:

1. A polymeric composition comprising units of a hydrophilic, arylsiloxy-containing monomer of formula

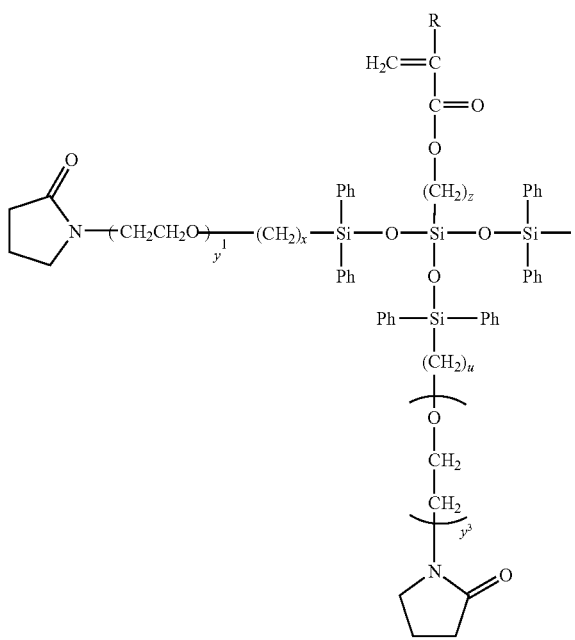

(III)

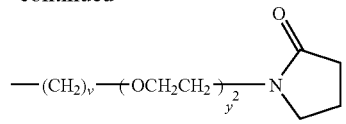

wherein R is hydrogen or $CH_3$; Ph is selected from the group consisting of unsubstituted and substituted phenyl groups; u, v, x, z, $y^1$, $y^2$, and $y^3$ are independently selected integers; $1 \leq u, v, x, z \leq 10$; and $0 \leq y^1, y^2, y^3 \leq 100$.

2. The polymeric composition of claim 1, wherein $1 \leq u, v, x, y \leq 4$ and $1 \leq y^1, y^2, y^3 \leq 20$.

3. The polymeric composition of claim 1, wherein Ph is a substituted phenyl group having a formula of

wherein $R^5$ is selected from the group consisting of —COOH, —$CH_2CH_2OH$, —$CH_2CH_2OCH_2CH_2OR$, —$CH_2CH(OH)CH_2OH$, —$C(O)NH_2$, and —$C(O)N(CH_3)_2$, wherein R is H or $CH_3$.

4. The polymeric composition of claim 1, further comprising units of at least one additional monomer selected from the group consisting of different hydrophilic monomers and hydrophobic monomers.

5. The polymeric composition of claim 4, wherein the additional monomer is selected from the group consisting of N,N'-dimethylacrylamide, glyceryl methacrylate, N-vinylpyrrolidone, and 2-hydroxyethyl methacrylate.

6. The polymeric composition of claim 4, wherein the additional monomer is selected from the group consisting of $C_1$-$C_{10}$ alkyl methacrylates, $C_1$-$C_{10}$ alkyl acrylates, $C_6$-$C_{40}$ arylalkyl acrylates, $C_6$-$C_{40}$ arylalkyl methacrylates, and other aromatic-based silicon-containing monomers.

7. The polymeric composition of claim 4, wherein the additional monomer is N,N'-dimethylacrylamide.

8. The polymeric composition of claim 4, wherein the additional monomer is selected from the group consisting of 2-phenylethyl acrylate, 2-phenylethyl methacrylate, and combinations thereof.

9. The polymeric composition of claim 4, further comprising units of a crosslinking agent.

10. The polymeric composition of claim 9, wherein the crosslinking agent is selected from the group consisting of ethylene glycol dimethacrylate; diethylene glycol dimethacrylate; ethylene glycol diacrylate; triethylene glycol dimethacrylate; triethylene diacrylate; allyl methacrylates; allyl acrylates; 1,3-propanediol dimethacrylate; 1,3-propanediol diacrylate; 1,6-hexanediol dimethacrylate; 1,6-hexanediol diacrylate; 1,4-butanediol dimethacrylate; 1,4-butanediol diacrylate; trimethylolpropane trimethacrylate; glycerol trimethacrylate; polyethyleneoxide mono- and di-acrylates; N,N'-dihydroxyethylene bisacrylamide; diallyl phthalate; triallyl cyanurate; divinylbenzene; ethylene glycol divinyl ether; N,N-methylene-bis-(meth)acrylamide; divinylbenzene; divinylsulfone; and combinations thereof.

11. The polymeric composition of claim 4, further comprising a UV light absorber selected from the group consisting of β-(4-benzotriazoyl-3-hydroxyphenoxy)ethyl acrylate; 4-(2-acryloxyethoxy)-2-hydroxybenzophenone; 4-methacryloyloxy-2-hydroxybenzophenone; 2-(2'-methacryloyloxy-5'-methylphenyl)benzotriazole; 2-(2'-hydroxy-5'-methacryloyloxyethylphenyl)-2H-benzotriazole; 2-[3'-tert-butyl-2'-hydroxy-5'-(3"-methacryloyloxypropyl)phenyl]-5-chlorobenzotriazole; 2-(3'-tert-butyl-5'-(3"-dimethylvinylsilylpropoxy)-2'-hydroxyphenyl]-5-methoxybenzotriazole; 2-(3'-allyl-2'-hydroxy-5'-methylphenyl)benzotriazole; 2-[3'-tert-butyl-2'-hydroxy-5'-(3"-methacryloyloxypropoxy)phenyl]-5-methoxybenzotriazole, and 2-[3'-tert-butyl-2'-hydroxy-5'-(3"-methacryloyloxypropoxy)phenyl]-5-chlorobenzotriazole.

12. The polymeric composition of claim 4, wherein the polymeric composition has a refractive index in a range from about 1.4 to about 1.6.

13. The polymeric composition of claim 4, wherein the polymeric composition has equilibrium absorbed water greater than about 4.5 percent by weight.

14. The polymeric composition of claim 4, wherein the polymeric composition has an elongation before break of greater than about 80 percent.

* * * * *